United States Patent [19]

Dunfee

[11] Patent Number: 5,718,509
[45] Date of Patent: Feb. 17, 1998

[54] MATERIALS DISPERSION APPARATUS WITH RELATIVELY SLIDABLE BLOCKS

[75] Inventor: William D. Dunfee, Hatboro, Pa.

[73] Assignee: Instrumentation Technology Associates, Inc., Exton, Pa.

[21] Appl. No.: 724,859

[22] Filed: Oct. 3, 1996

[51] Int. Cl.$^6$ .................................................. B01F 13/00
[52] U.S. Cl. ...................... 366/143; 366/349; 206/219; 206/221; 220/502
[58] Field of Search ................................. 366/130, 143, 366/340, 341, 347, 349, 219; 206/219, 221; 220/502

[56] References Cited

U.S. PATENT DOCUMENTS

| | | | |
|---|---|---|---|
| 2,510,211 | 6/1950 | Cleary | 206/219 X |
| 4,534,569 | 8/1985 | Dourdeville et al. | 366/341 X |

*Primary Examiner*—Charles E. Cooley
*Attorney, Agent, or Firm*—Howson and Howson

[57] ABSTRACT

A dispersion apparatus for microgravity experiments comprises two blocks in face to face relationships, each having an array of wells for containing liquids and being relatively slidable so that the wells in one of the blocks can be brought into communication with corresponding wells in the other block. The blocks are held together by a retention mechanism which imparts a substantially constant pressure at the interface between the blocks. The retention mechanism comprises rails situated in grooves in the outside surfaces of the blocks and a series of coiled tension springs connected to the rails. The springs, acting through the rails, apply pressure to the blocks, but impart almost no force tending to cause the blocks to slide relative to each other. The blocks are guided by guide plates which cooperate with grooves in the mating faces of the blocks. An embodiment in which one of the blocks has a row of wells with optical windows, utilizes a guided camera to observe the interior of the wells.

14 Claims, 6 Drawing Sheets

MATERIALS DISPERSION APPARATUS WITH RELATIVELY SLIDABLE BLOCKS

BACKGROUND OF THE INVENTION

1. Field of the Invention

The invention relates in general to the mixing of fluid samples, and in particular to an apparatus for mixing a plurality of sets of fluid samples during experiments conducted in the microgravity environment of space.

2. Description of Prior Art

Mixing of fluids is being conducted in orbital flight to take advantage of the effects of reduced convection and sedimentation inherent in a greatly reduced gravitation environment. A portion of that experimentation, in disciplines such as cell biology, plant biology, macro-molecular chemistry, inorganic crystallography and micro-encapsulation of medicinal drugs, requires mixing of two or more liquids combined in precise proportions using diffusion or partial diffusion. A typical example of a liquids mixing experiment conducted in microgravity is the mixing in space of a protein substance such as aldolase from rabbit with a salt solution to produce crystals of higher structural quality than those similarly produced on earth, where the mixing of the liquids is influenced by gravity. Since there are large numbers of possible combinations of experimental parameters, such as the concentration of salts used in crystal growth, many experimental samples must be collected during each space flight to attain statistically significant experimental results.

The need for a multiplicity of data points, coupled with the need for effective utilization of the limited available space onboard a space vehicle and the limited number of space flights, dictates that the apparatus used in liquid mixing experiments be compact to yield a large number of data points per unit of volume. Furthermore, since many of the experimental liquids are potentially toxic to the ground and space crews handling the equipment, the equipment must contain the experimental liquids without allowing any external leakage during the experimentation.

The prior art includes an apparatus known as a "Materials Dispersion Apparatus" or "MDA", made and used by Instrumentation Technology Associates of Exton, Pa. The MDA has been used in microgravity investigations during several space flights. It comprises a pair of blocks of synthetic resin, in each of which an array of holes (or wells) has been drilled. The blocks are placed in face-to-face relationship, so that the faces containing the wells are pressed into contact with each other. A thin layer of a high-viscosity lubricant serves as a sealant against leakage of the liquids that are contained within the wells. In the initial position of the blocks relative to each other, the wells in one block are misaligned with the wells in the other block, and the liquids contained within the wells do not communicate with each other. The "microgravity" position is achieved by sliding the blocks relative to each other so that the wells of one block come into register with the wells of the other block. When the wells are in register, there is communication between pairs of wells, each pair consisting of one well in one of the blocks and a corresponding well in the other block. In the microgravity position, the liquids in the communicating pair of wells mix through the process of diffusion.

In the use of the previously known MDA, a series of steps is carried out which results in variations in the pressure at the interface between the two blocks. Before the wells in the blocks are filled with liquids, a predetermined weight is placed on the blocks to provide the proper pressure to regulate the thickness of lubricant at the interface between the blocks. During the filling of the wells, the weight is removed to allow access to the well openings. During flight preparation, the pair of blocks is placed in a housing which, upon closing, applies a specified pressure to the interface between the blocks. The blocks remain in the housing during flight. Finally, after flight, the housing is opened, releasing the pressure at the interface. Because of the variations in the pressure resulting from these steps, there is significant risk of leakage at the interface between the blocks.

Another drawback of the previously known MDA is that the blocks are firmly held together only when they are located inside their housing. Consequently, it is difficult to avoid leakage while filling the wells, and it is difficult to carry out bench tests on the blocks.

SUMMARY OF THE INVENTION

An important object of this invention is to provide an improved materials dispersion apparatus which is capable of being filled with the experimental liquids before flight, operated to combine the liquids, and unloaded after flight with a minimum risk of leakage.

Another object of the invention is to provide a compact, simple, inexpensive and reliable apparatus for mixing a plurality of liquid samples in the microgravity environment of space.

Still another object of the invention is to provide a materials dispersion apparatus comprising two relatively slidable blocks which can be readily bench tested outside their housing.

Still another object of the invention is to provide a simple and effective way to monitor or record the experiments taking place in selected wells of the blocks.

Briefly, the susceptibility of the apparatus to leakage is reduced by reducing the variations in pressure at the interface of the blocks. This is accomplished by a block-retaining mechanism comprising an arrangement of tension springs and rails which apply a substantially constant pressure, holding the blocks in face-to-face relationship with each other. The block-retaining mechanism maintains this substantially constant pressure on the blocks during filling of the wells, throughout orbital flight, and during recovery of the liquid samples.

In flight, the blocks and their retaining mechanism are contained within a box-like housing which is sealed by a cover plate. The springs maintain the blocks firmly in contact with each other both while they are inside the housing and while they are outside the housing.

The apparatus in accordance with the invention comprises first and second blocks in face-to-face relationship, with surfaces in contact with each other. Each of the contacting surfaces has a plurality of fluid-containing wells having openings in the surface of the block and extending into the interior of the block. The blocks are relatively slidable so that the wells of each block can be moved from a position in which they are closed off by the surface of the other block into a position in which they are in register with corresponding wells of the other block. The improvement comprises means for exerting a pressure on the blocks to maintain their surfaces in contact with each other. The pressure-exerting means comprises a plurality of tension springs and means for connecting each of the springs to both blocks, whereby the blocks are maintained in face-to-face relationship with each other while the blocks are not in a container.

The pressure exerting means exerts a substantially constant pressure on the blocks both while the blocks are in the housing and while they are being handled outside the housing. Consequently, the likelihood of leakage as a result of pressure variations is significantly reduced.

Preferably, the springs are sufficiently long that the net force they exert in the directions of relative sliding motion of the blocks is substantially zero, whether the wells are in or out of register with one another.

In a preferred embodiment of the invention, the meeting surfaces of the blocks are planar, and at least one of the blocks has an opposite face with at least one groove extending in a direction parallel to the planar surfaces. The springs are attached to a rail means comprising a rail located in each groove so that the rail means distributes the forces exerted by the springs the block.

The preferred materials dispersion apparatus also includes guide means for restricting the relative sliding movement of the blocks to forward and reverse movement along a straight line.

For monitoring the experiments, at least one of the blocks may be provided with a row of wells aligned in a direction parallel to its side wall, each well in the row having an optically transparent window extending to the side wall. A camera is guided for movement in a direction parallel to the side wall and indexed from one window to the next so that it can receive an image of the interior of each of the wells in the row individually.

Preferably, the optically transparent window for each well comprises a threaded opening extending from the side wall to the well, and an insert threaded into the opening, the insert having a hole extending through it in the direction from the side wall to the well, and having a transparent sealing element adjacent to the well for preventing flow of fluid from the well through the hole.

As a further precaution against leakage, to supplement the sealing effect of the thin lubricant coating on the meeting surfaces of the blocks, the surface of one of the blocks has a groove surrounding the an area thereof containing the well openings, and a compressible seal disposed in the groove. The seal is held in compression by the surface of the other block.

DETAILED DESCRIPTION

Figure 1A:
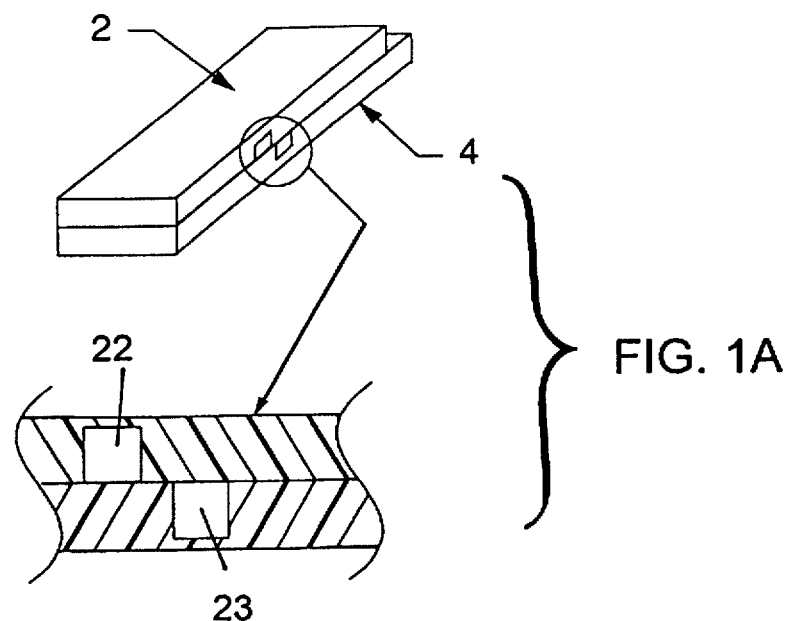
FIGS. 1A and 1B are schematic diagrams illustrating how fluids are mixed with each other by moving well blocks relative to each other to align fluid-containing wells.
Figure 1B:
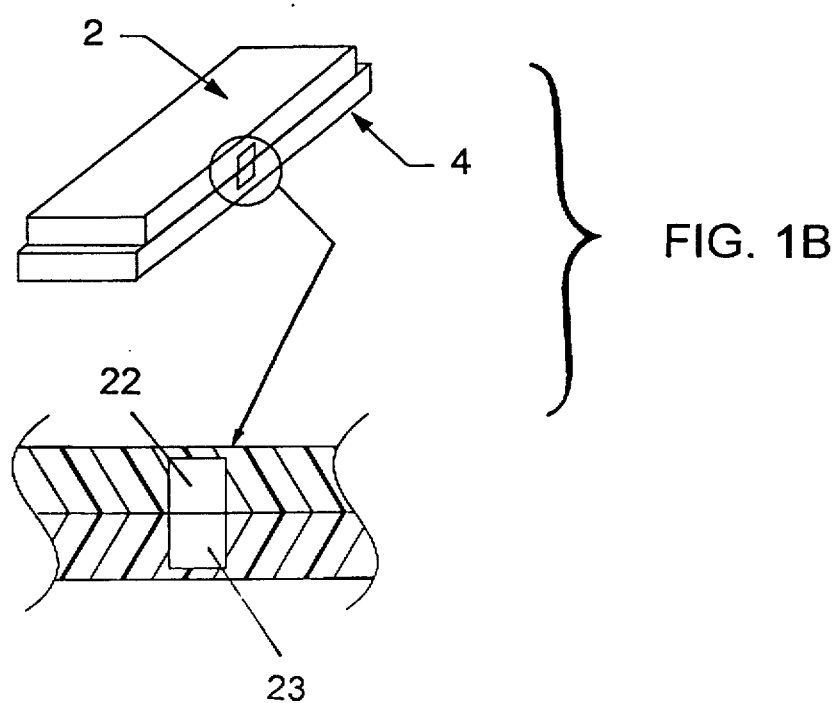

FIG. 1A shows an upper block 2 and a lower block 4 positioned in face-to-face relationship with each other and in the initial or "launch" position, in which the wells 22 in the upper block are misaligned with the wells 23 in the lower block. Because the wells are misaligned, the fluids contained in the wells do not communicate with each other. Each well is sealed by the surface of the opposite block. When the upper block 2 is moved to the "microgravity" position, as depicted in FIG. 1B, the openings of the wells are brought into register with each other so that there is fluid communication between the wells. In the microgravity position, the fluids in the communicating wells come into contact with each other at an interface and mix through the process of diffusion.

Figure 2:
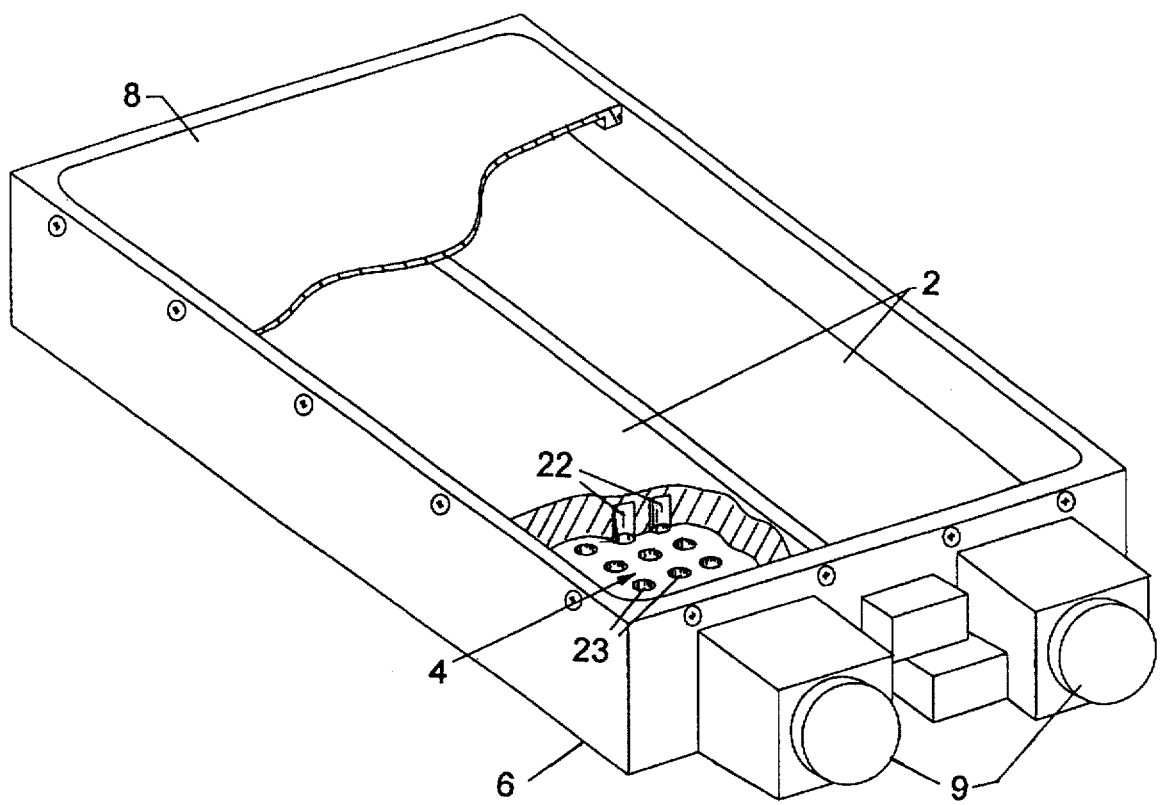
FIG. 2 is an isometric view, partially broken away, showing a housing containing two sets of blocks in accordance with the invention.

FIG. 2 shows the configuration of a typical embodiment of the invention, comprising two sets of blocks 2 and 4, each having a flat surface and a plurality of wells 22 and 23, for containing liquid samples. Each of the wells has an opening in the flat surface of its block and extends into the interior of the block. In the preferred embodiment the blocks are made of synthetic resin, for example an acetal polymer known by the trademark DELRIN, or a polycarbonate.

The upper and lower blocks of each set are disposed in face-to-face relationship with their flat surfaces in contact with each other. A thin layer of a suitable lubricant, for example a silicone grease, is positioned between the meeting flat surfaces to seal the interface between the surfaces.

The sets of blocks are situated in a box-like containment housing 6, sealed by a removable cover 8. The containment housing is provided with a pair of linear actuators 9, arranged to apply driving force to the upper blocks, causing them to slide relative to the lower blocks in the manner depicted in FIGS. 1A and 1B.

At a prescribed time, for each set of blocks, the corresponding actuator 9 moves the upper block 2 relative to the lower block 4 from a position in which the wells are closed off to a position in which the wells in the upper block 2 are in register with the wells in the lower block 4. When the wells are in register with one another, fluid communication takes place between the wells, and the fluids contained within pairs of wells are mixed together.

The principal improvement afforded by this invention is the block retention mechanism, which applies the appropriate pressure between the upper and lower blocks, maintaining contact between the blocks.

The block retention mechanism allows the wells to be filled with sample fluids, sealing of the wells, placement of the sets of blocks within the housing 6, and removal of the blocks from the housing after flight, all without changing the pressure between the blocks and thus compromising the sealing of the wells. The block retention mechanism is aided by a guide mechanism for restricting the relative sliding movement of the blocks in the direction parallel to their direction of elongation.

Figure 3:
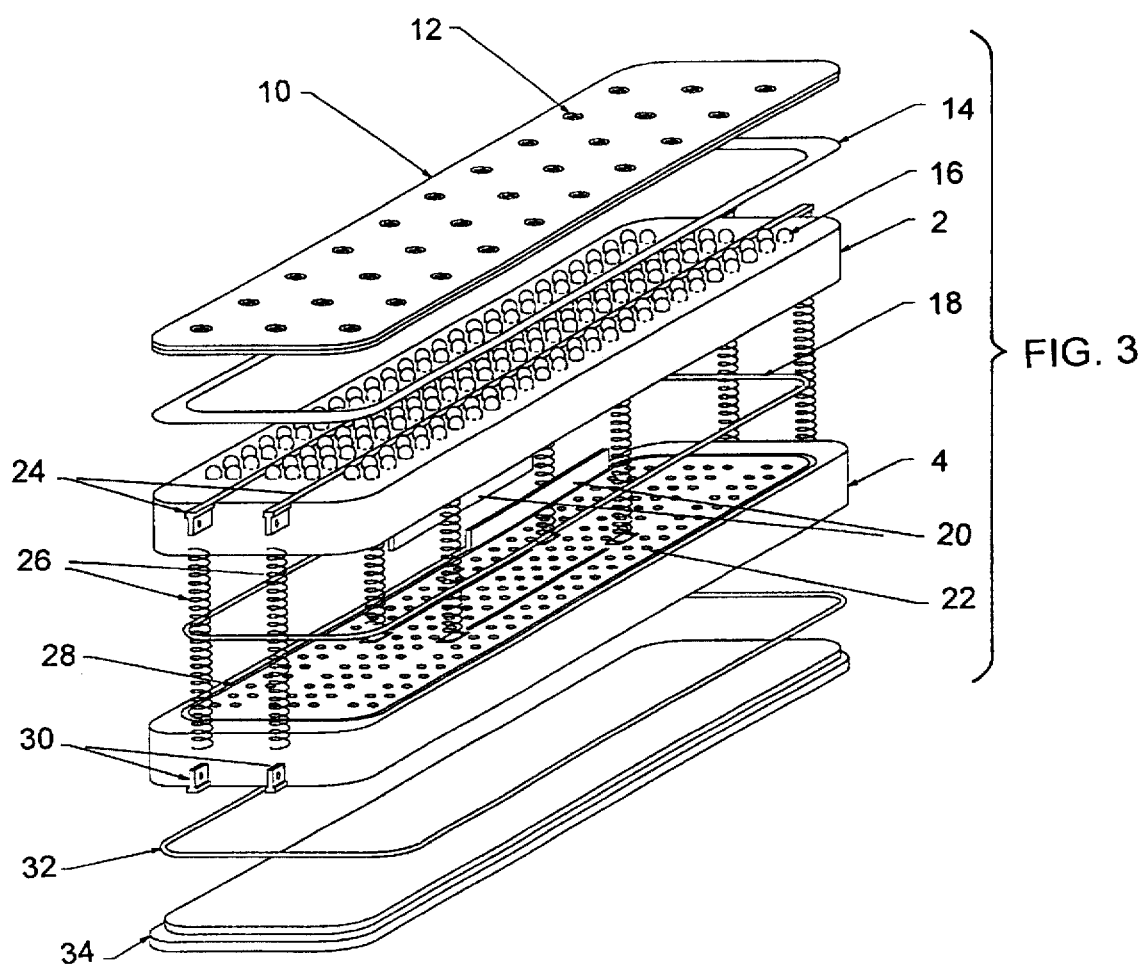
FIG. 3 is an exploded view showing the blocks and the retaining mechanism.

The block retention mechanism, depicted in FIG. 3, comprises four pairs of coiled tension springs 26. Together, these springs apply a pressure of about 0.5 pound per square inch at the interfacing flat surfaces of the blocks.

Two rails 24 are disposed in grooves extending lengthwise in the top face of the upper block 2 and two similar rails 30 are disposed in grooves extending lengthwise along the bottom face of the lower block 4. These rails allow attachment of the tension springs to the blocks, and distribute compressive force along the lengths of the blocks. The pairs of springs at the ends of the assembly are attached to the ends of the rails. The intermediate springs, which are stronger than the end springs, extend through elongated holes 25 in the blocks (see FIG. 4) and the connections of the intermediate springs to the rails are located inside these holes. The elongation of the holes allows the springs to tilt as the blocks are moved relative to each other.

Guide plates 20, each being a metal plate with a rectangular cross-section, fit into opposing slots in the upper and lower blocks. The cooperation of the plates and slots restricts the relative motion of the blocks to directions in a straight line, parallel to the direction of elongation of the blocks.

An upper plate 10 is attached by screws 12 to the upper block 2 and retains balls 16, which seal the wells 22 in the upper block 2 they have been filled with liquid. A gasket 14 ensures that no liquid escaping from the wells past the balls 16 will leak to the outside of the block assembly. A lower plate 34 is attached to the lower block 4 and a gasket 32 provides a seal against any leakage of fluid passing through the spring holes in the lower block.

A compressible gasket 18, of synthetic rubber or other suitable material is disposed in a groove 28, which surrounds the area of the upper surface of the lower plate in which the openings of the wells are located.

The ratio of length of the tension springs to the length of the relative movement of the upper and lower blocks is sufficiently high that the force component exerted by the springs in the direction parallel to the lengths of the blocks (i.e., in the direction of relative motion of the upper and lower blocks is substantially zero, both in the initial relative position and in the "microgravity" position. This also maintains a substantially constant compressive force on the blocks as the springs tilt. The relative cross-sectional dimensions of the gasket 18 and groove 28 are such that, when the gasket is compressed against the upper block 2, the surfaces of the blocks can come into in contact with each other with the proper pressure to ensure sealing of the wells 22 by the lubricant, and sealing of the outer periphery of the blocks by the gasket.

Figure 4:
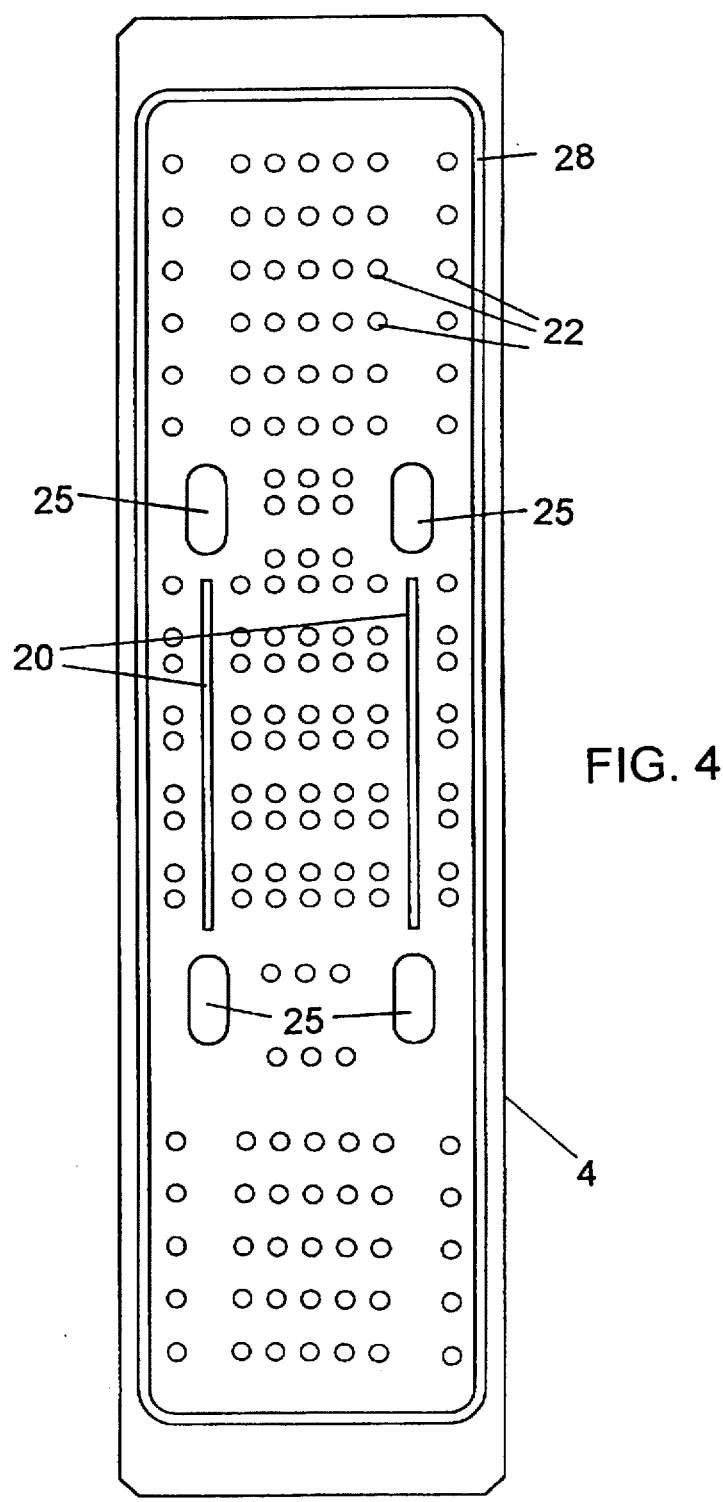
FIG. 4 is a plan view of one of the blocks showing a typical pattern of wells.

FIG. 4 is a plan view of the lower block 4 showing a typical arrangement of wells 22, guide plates 20, and block interface groove 28. The wells in the lower block 4 may be threaded at their inner ends to allow threaded plugs to be inserted, if needed, to vary the depths of the wells, in order to fit well volume requirements of specific experiments.

Figure 5:
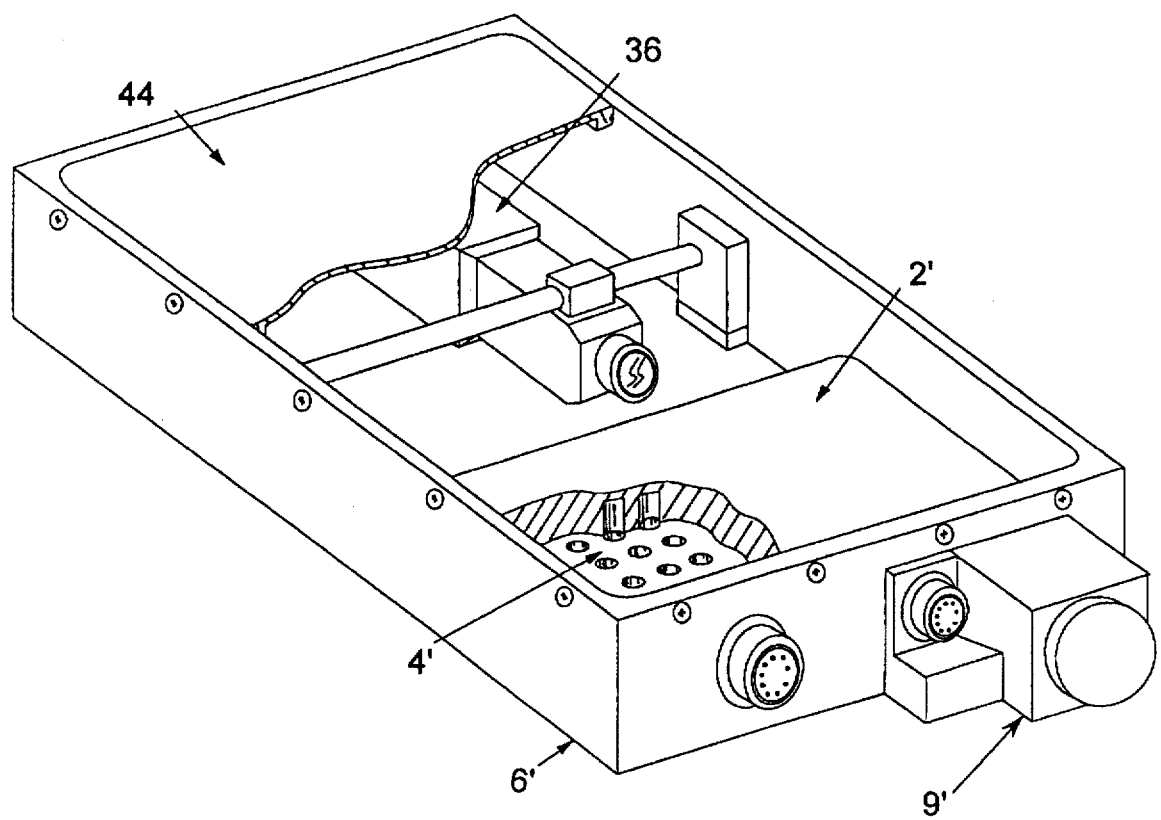
FIG. 5 is an isometric view, partially broken away, showing a housing containing a set of blocks, a camera and a camera guide.

An alternate embodiment of the invention is used in applications requiring visualization of the contents of the wells during and after mixing of liquids. FIG. 5 shows a configuration in which an upper block 2' and a lower block 4' are placed within a housing 6' having a cover 44. The blocks are located at one end of the housing with their direction of elongation perpendicular to the optical axis of a camera 36 which has a mechanism capable of guiding the camera and controlling the position of its optical field relative to the blocks. The lower block has a row of wells aligned in a direction parallel to its side wall facing the camera. The upper block is driven relative to the lower block by an actuator 9. The actuator mechanism differs from those in FIG. 9 in that it drives the upper block from the side. The upper block moves parallel to the direction of its longest dimension.

Figure 6:
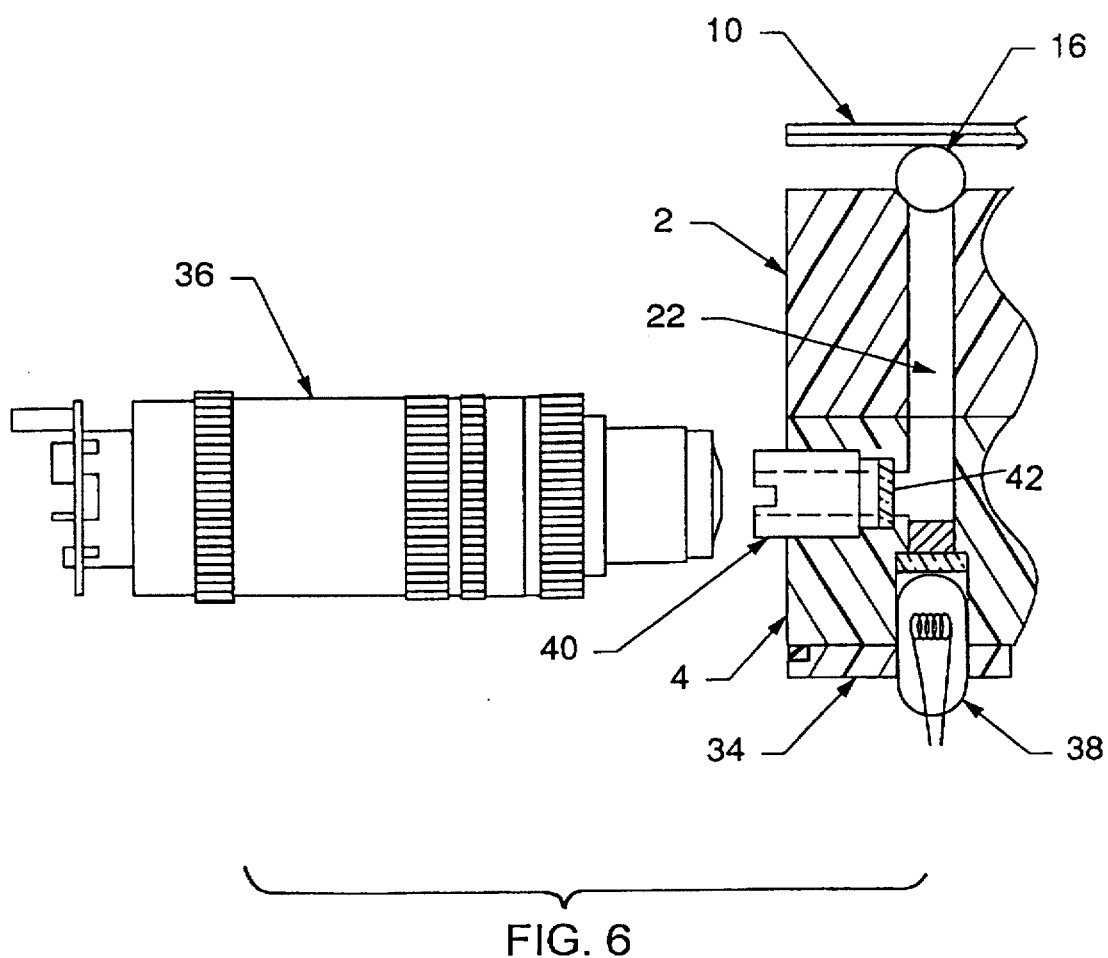
FIG. 6 is a fragmentary sectional view showing shows details of the window allowing the contents of a well to be observed, and also showing the camera.

As shown in FIG. 6, each well in the row contains an optically transparent window comprising an insert 40 threaded into an opening on the lower block 4' extending from the side wall to the well 23'. The insert has a central passage and a transparent sealing element 42 adjacent to the well 23' for preventing flow of fluid from the well though the hole. The optically transparent window allows the camera to produce an image of a portion of the interior of the well. Each well in the row has a light source 38 for the illumination of its interior. The camera is indexed along its guide from one window to the next, allowing the camera to receive image of the interiors of the wells sequentially. The embodiment of FIGS. 5 and 6, of course preferably utilizes a block retention mechanism comprising rails and springs, similar to that illustrated in FIG. 3.

As will be apparent from the foregoing description, the block-retaining mechanism, utilizing springs and rails, substantially eliminates varying compression of the well blocks as a potential cause of leakage. Furthermore, since the block retaining mechanism is independent of the housing, it maintains the desired pressure forcing the blocks together even while the blocks are outside the housing. Consequently it is possible to load the wells, and also to carry out bench tests on the block assembly, while the constant compressive force is being maintained.. In the second embodiment, the optical windows in the block and the camera assembly allow visualization and recording of the mixing taking place in those wells having windows.

Various modifications can be made to the apparatus described. For example, while the apparatus is primarily useful in mixing liquids, it can be used to mix gases with each other or with liquids, and can be used in various experiments such as osmotic dewatering, magnetic mixing, crystal growth, etc. The actuators can be reversible. Furthermore, with appropriate arrangements of wells and with appropriate block movement controls, experiments can be carried out in multiple steps, e.g. experiments in which the wells in a lower block are exposed, in successive steps, to different upper blocks. The wells, of course can be provided in various numbers, sizes and configurations, depending on experimental requirements.

The foregoing description of typical embodiments of the invention serves the purposes of illustration and description, and it not intended to be exhaustive nor to limit the invention to the precise form disclosed. Many modifications and variations are possible, and it is intended that the scope of the invention be limited not by this detailed description, but rather by the appended claims.

I claim:

1. Apparatus for mixing fluids comprising first and second blocks, each block having a surface and a plurality of wells having openings in said surface and extending into the interior thereof, each of the wells being adapted to contain a fluid, and in which the blocks are disposed in face-to-face relationship, with said surfaces in contact with each other, and the blocks are relatively slidable so that the wells of each block can be moved from a position in which they are closed off by the surface of the other block into a position in which they are in register with corresponding wells of the other block, wherein the improvement comprises means for exerting a pressure on said blocks to maintain said surfaces in contact with each other, the pressure-exerting means comprising a plurality of tension springs and means for connecting each of said springs to both blocks, whereby the blocks are maintained in face-to-face relationship with each other while the blocks are not in a container.

2. Apparatus according to claim 1 in which the pressure-exerting means exerts a substantially constant pressure on the blocks.

3. Apparatus according to claim 1 in which the springs are sufficiently long that the net force exerted by the springs in the directions of relative sliding motion of the blocks is substantially zero in both of said positions.

4. Apparatus according to claim 1 in which said surfaces of the blocks are planar, and in which at least one of the blocks has a face opposite its said surface, and rail means comprising an elongated rail extending along said face, and in which the springs are connected to said at least one block by attachment to said rail means, whereby said rail means distributes the forces exerted by the springs to said at least one block.

5. Apparatus according to claim 4 comprising guide means for restricting the relative sliding movement of the blocks to forward and reverse movement along a straight line.

6. Apparatus according to claim 5 in which said at least one of the blocks has a hole extending there through and at least one of the springs extends into the hole and is connected to said rail means therein, the hole being elongated in a direction parallel to the direction of elongation said rail, whereby said at least one of the springs can tilt as the blocks move relative to each other.

7. Apparatus according to claim 1 in which said surfaces of the blocks are planar, and in which at least one of the blocks has a face opposite its said surface, at least one elongated groove in said face extending in a direction parallel to said planar surfaces, and rail means comprising a rail located in each said groove, and in which the springs are connected to said at least one block by attachment to said rail means, whereby said rail means distributes the forces exerted by the springs said at least one block.

8. Apparatus according to claim 7 comprising guide means for restricting the relative sliding movement of the blocks to forward and reverse movement along a straight line.

9. Apparatus according to claim 8 in which said at least one of the blocks has a hole extending there through and at least one of the springs extends into the hole and is connected to said rail means therein, the hole being elongated in a direction parallel to the direction elongation of said at least one groove, whereby said at least one of the springs can tilt as the blocks move relative to each other.

10. Apparatus according to claim 1 in which one of said blocks has a side wall and a row of wells aligned in a direction parallel to said side wall, and in which each of said wells has an optically transparent window extending to said side wall, and including a camera, means for guiding the camera for movement in a direction parallel to said side wall and means for indexing the camera from one window to the next, whereby the camera can receive an image of the interior of each of the wells in said row individually.

11. Apparatus according to claim 10 in which the optically transparent window for each well in said row of wells comprises an opening extending from the side wall to the well, and an insert located in the opening, the insert having a hole extending through it in the direction from the side wall to the well, and having a transparent sealing element adjacent to the well for preventing flow of fluid from the well through said hole.

12. Apparatus according to claim 10 in which the optically transparent window for each well in said row of wells comprises a threaded opening extending from the side wall to the well, and an insert threaded into the opening, the insert having a hole extending through it in the direction from the side wall to the well, and having a transparent sealing element adjacent to the well for preventing flow of fluid from the well through said hole.

13. Apparatus according to claim 10 including illuminating means at the bottom of each well in said row for illuminating the contents thereof.

14. Apparatus according to claim 1 in which said surfaces of the blocks are coated with a lubricant, and in which said surface of one of the blocks has a groove surrounding the an area thereof containing the well openings, and a compressible seal disposed in said groove, and held in compression by the said surface of the other block.

* * * * *